United States Patent [19]

Mikkelsen

[11] Patent Number: Plant 6,013

[45] Date of Patent: Sep. 15, 1987

[54] BEGONIA PLANT NAMED CHEERS

[75] Inventor: James C. Mikkelsen, Ashtabula, Ohio

[73] Assignee: Mikkelsens, Inc., Ashtabula, Ohio

[21] Appl. No.: 807,332

[22] Filed: Dec. 10, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A begonia plant named Cheers particularly characterized as to uniqueness by the combined characteristics of rose-red flower color, strong and upright petioles which support flowers above foliage, double flower form, floriferous habit, fast growth with good branching, and by its adaptability to 10 or 15 cm. pots.

1 Drawing Figure

1

The present invention relates to a new and distinctive cultivar of begonia plant, botanically known as *hiemalis×begonia Fotsch,* and known by the cultivar name Cheers.

The new cultivar was discovered by me as a seedling from a controlled crossing of Mikkelsen tuberous begonia No. 78-111-32 as the seed parent with Socotrana begonia selection No. 74-176s as the pollen parent.

Asexual reproduction by stem and/or leaf cuttings has reproduced the unique features of the new cultivar through successive propagations.

The following characteristics distinguish Cheers from both its parent cultivars and other begonias commercially known and used in the floriculture industry:

1. The upper surface of the leaves is a darker green than Hilda (U.S. Plant Pat. No. 5,532), but similar in color to Aphrodite Cherry Red (U.S. Plant Pat. No. 3,319) and Connie (U.S. Plant Pat. No. 5,169). The leaf size is similar for all three.

2. The lower surface of young leaves is yellow-green with a touch of red, similar to Hilda and Aphrodite Cherry Red, but differing from Connie which is almost reddish-green on the under side.

3. The leaf texture is similar to Connie; the texture of Hilda and Aphrodite Cherry Red is coarser.

4. The stem strength and diameter is similar to Connie, slightly greater than Hilda, and much greater than Aphrodite Cherry Red. The petioles are very strong and the flowers upright like Connie and Hilda, while the stems of Aphrodite Cherry Red allow the flowers to hang because the petioles are weaker.

5. The stem color of Cheers is mostly green like Aphrodite Cherry Red, with Hilda and Connie having red pigment in the stems. All have some red pigment in the petioles.

6. Cheers has a bright rose flower while Aphrodite Cherry Red is duller in color. Connie is a red-rose and Hilda is crimson.

7. The flower size of Cheers is equal to Connie and a little larger than Hilda and Aphrodite Cherry Red. All are about equal in the amount of flowers produced.

8. The rose flower form is not as pronounced as Connie and Aphrodite Cherry Red, nor as double as Hilda.

9. Strong stems and petioles result in flowering at top of plant, making Cheers very suitable for both 10 and 15 cm. pots.

10. Cheers propagates well from both stem and leaf cuttings.

2

The accompanying colored photograph illustrates in perspective the overall appearance of Cheers showing the colors as true as it is reasonably possible to obtain in a colored reproduction of this type.

The following is a detailed description of my new begonia cultivar based on plants produced under commercial practices in Ashtabula, Ohio. Color references are made to The Royal Horticultural Society Colour Chart except where general terms of ordinary dictionary significance are used.

Parentage: Controlled cross of tuberous begonia 78-111-32×Socotrana begonia 74-176s.

Propagation:

(A) *Type cutting.*—Leaf cuttings.

(B) *Time to root.*—3–4 weeks at 21° C. (temperature of growing medium).

(C) *Rooting habit.*—Abundant, fibrous, fine.

(D) *Time for shoot development.*—9 weeks in summer to 13 weeks in winter to obtain shoots of approximately 4–5 cm. in length.

Plant description:

(A) *Form.*—Upright, with good stem strength for self-support. Growing and scheduling practices can result in a medium size plant in a 10 cm. pot to a large plant in a 15 cm. pot.

(B) *Habit of growth.*—Fast grower with good branching from base of plant when pinched. Generally, vegetative shoots are formed at the basal nodes and flower shoots at the higher nodes.

(C) *Foliage.*—Leaves simple, alternate, borne on strong petioles 6 mm. in diameter on mature leaves. (1) Size: Strongly varying based on the position on the plant and environmental conditions; up to 10×14 cm. when full grown. (2) Shape: Ovate. (3) Texture: Leathery, glabrous. (4) Margin: Serrated. (5) Color: Young foliage top side, yellow-green 146A with reddish tinge at margins. Young foliage under side, yellow-green 148B with reddish coloration near margins. Mature foliage top side, yellow-green 147A. Mature foliage under side, yellow-green between 147B and 148B. (6) Veination: Palmate with 6–7 main veins.

Flowering description:

(A) *Flowering habits.*—Flowers in cymes, generally consisting of two branches after the first flower; each of the branches generally branch again.

(B) *Natural flowering season.*—Throughout the year; plants will flower at an earlier stage of development under short day conditions.

(C) *Flower buds.*—Oblong, up to 18 mm. long and 25 mm. wide before opening. Tepals are entire around the margins. Color between 46A and 45B for immature buds to near 52A just before opening.

(D) *Flowers borne.*—On strong upright peduncles ranging in color from green near the main branch to reddish near the flower; 5 mm. in diameter at the main peduncle.

(E) *Quantity of flowers.*—Average of 9 or more flowers per peduncle, opening up in sequence as the cyme opens.

(F) *Tepals.*—(1) Shape: Nearly round with margins flat and entire. (2) Color top side in fall when opening: slightly deeper than red 52A, fading to 52B–C; under side 50A. (3) Number of tepals: Varies with doubleness of flowers, but more than 8. (4) Size of tepals: 35 mm. in diameter when fully opened. (5) Flower size: 50 to 60 mm. in diameter when fully opened.

(G) *Reproductive organs.*—(1) Stamens: None, as plant is full double with all anthers appearing as petals. No pollen. (2) Pistels: None observed to date.

Disease resistance: To date Cheers has shown good disease resistance to powdery mildew.

I claim:

1. A new and distinct cultivar of begonia named Cheers, as described and illustrated, and particularly characterized by its rose-red flower color, strong and upright petioles which support flowers above foliage, double flower form, floriferous habit, fast growth with good branching, and by its adaptability to 10 or 15 cm. pots.

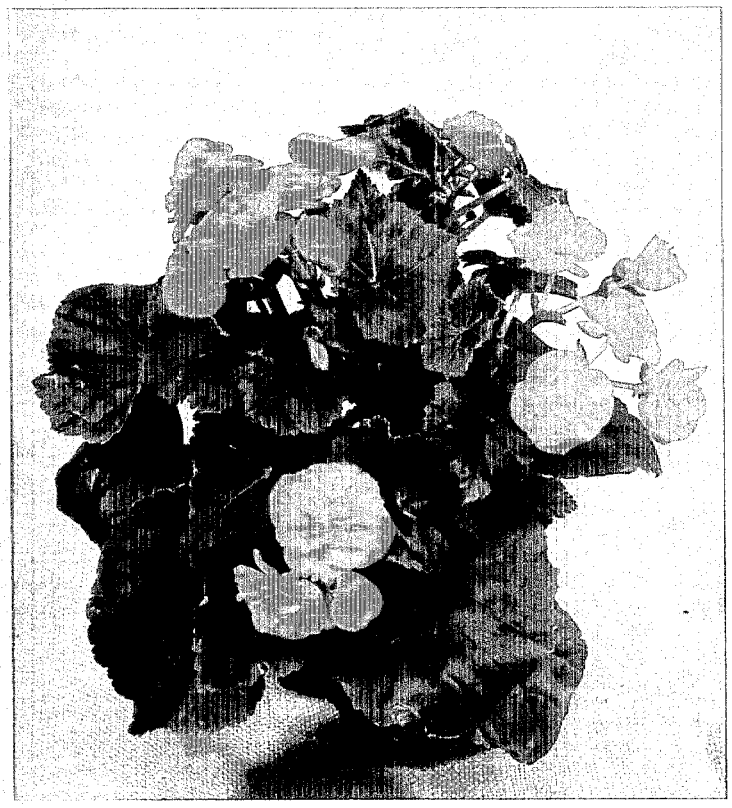

* * * * *